(12) United States Patent
Sue et al.

(10) Patent No.: US 12,153,347 B2
(45) Date of Patent: Nov. 26, 2024

(54) ORGANICALLY MODIFIED METAL OXIDE NANOPARTICLE, METHOD FOR PRODUCING THE SAME, EUV PHOTORESIST MATERIAL, AND METHOD FOR PRODUCING ETCHING MASK

(71) Applicant: NATIONAL INSTITUTE OF ADVANCED INDUSTRIAL SCIENCE AND TECHNOLOGY, Tokyo (JP)

(72) Inventors: Kiwamu Sue, Tsukuba (JP); Sho Kataoka, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 883 days.

(21) Appl. No.: 17/256,027

(22) PCT Filed: Jun. 19, 2019

(86) PCT No.: PCT/JP2019/024286
§ 371 (c)(1),
(2) Date: Dec. 24, 2020

(87) PCT Pub. No.: WO2020/004172
PCT Pub. Date: Jan. 2, 2020

(65) Prior Publication Data
US 2021/0149299 A1    May 20, 2021

(30) Foreign Application Priority Data

Jun. 29, 2018 (JP) ................................ 2018-124526
Feb. 8, 2019 (JP) ................................ 2019-021317

(51) Int. Cl.
*G03F 7/004* (2006.01)
*C07F 7/00* (2006.01)
(Continued)

(52) U.S. Cl.
CPC ............ *G03F 7/0042* (2013.01); *C07F 7/003* (2013.01); *H01L 21/0274* (2013.01); *G03F 7/2004* (2013.01); *G03F 7/325* (2013.01)

(58) Field of Classification Search
None
See application file for complete search history.

(56) References Cited

U.S. PATENT DOCUMENTS

2008/0242745 A1   10/2008 Morimura ........................ 516/90
2017/0009062 A1*   1/2017 Kimura ..................... C08K 9/06
2017/0031244 A1*   2/2017 Thackeray .............. G03F 7/162

FOREIGN PATENT DOCUMENTS

JP    2001-072716 A    3/2001
JP    2008-044835 A    2/2008
(Continued)

OTHER PUBLICATIONS

Translated Description of Hirota (JP) (Year: 2013).*
(Continued)

*Primary Examiner* — Sean M DeGuire
*Assistant Examiner* — Andrew Preston Traywick
(74) *Attorney, Agent, or Firm* — OSTROLENK FABER LLP

(57) ABSTRACT

An organically modified metal oxide nanoparticles that can be produced by a simple method and can increase the sensitivity and resolution of a resist material. The EUV photoresist material contains organically modified metal oxide nanoparticles and a solvent. The organically modified metal oxide nanoparticles include a core, a first modification group, and a second modification group. The core includes a plurality of metal atoms and a plurality of oxygen atoms bonded to the plurality of metal atoms. The first modification group is a carboxylic acid carboxylate ligand coordinated to the core. The second modification group is a carboxylic acid carboxylate ligand coordinated to the core and having a (Continued)

smaller molecular weight than the first modification group and/or an inorganic anion smaller in size than the first modification group.

13 Claims, 2 Drawing Sheets

(51) Int. Cl.
  *G03F 7/20* (2006.01)
  *G03F 7/32* (2006.01)
  *H01L 21/027* (2006.01)

(56) References Cited

FOREIGN PATENT DOCUMENTS

| | | | | |
|---|---|---|---|---|
| JP | 2008-247619 A | | 10/2008 | |
| JP | 2009-096681 A | | 5/2009 | |
| JP | 2012-185484 A | | 9/2012 | |
| JP | 2013216858 A | * | 10/2013 | ............... B32B 9/00 |
| JP | 2015-108781 A | | 6/2015 | |
| JP | 2015-157807 A | | 9/2015 | |
| JP | 2017-036435 A | | 2/2017 | |
| JP | 2017-173537 A | | 9/2017 | |
| KR | 2014117352 A | * | 10/2014 | ............... B32B 9/00 |
| TW | 201336786 A | | 9/2013 | |

OTHER PUBLICATIONS

Translated Application of Hirota (KR) (Year: 2014).*
International Search Report mailed Sep. 3, 2019 in corresponding PCT International Application No. PCT/JP2019/024286.
Written Opinion mailed Sep. 3, 2019 in corresponding PCT International Application No. PCT/JP2019/024286.
Office Action mailed Apr. 15, 2020 in corresponding Taiwanese Patent Application No. 108121485.
Jing Jiang et al., Journal of Photopolymer Science and Technology, 2014, 27(5):663-666.
Jing Jiang et al., Journal of Photopolymer Science and Technology, 2015, 28(4):515-518.
Marie Kryask et al., Journal of Photopolymer Science and Technology, 2013, 26(5):659-664.
Christopher K. Ober et al., Journal of Photopolymer Science and Technology, 2018, 31(2):261-265.
Seiji Takahashi et al., Journal of Photopolymer Science and Technology, 2018, 31(2):257-260.
Fabrice Stehlin et al., Journal of Materials Chemistry C, 2014, 2:277-285.
Li et al.: "Studying the Mechanism of Hybrid Nanoparticle Photoresists: Effect of Particle Size on Photo-Patterning", *Chemistry of Materials*, 2015, 27, 14, 5027-5031.

* cited by examiner

ORGANICALLY MODIFIED METAL OXIDE NANOPARTICLE, METHOD FOR PRODUCING THE SAME, EUV PHOTORESIST MATERIAL, AND METHOD FOR PRODUCING ETCHING MASK

CROSS-REFERENCE TO RELATED APPLICATIONS

The present application is a 35 U.S.C. §§ 371 national phase conversion of PCT/JP2019/024286, filed Jun. 19, 2019, which claims priority to Japanese Patent Application No. 2018-124526, filed Jun. 29, 2018, and Japanese Patent Application No. 2019-021317, filed Feb. 8, 2019, the contents of which are incorporated herein by reference. The PCT International Application was published in the Japanese language.

TECHNICAL FIELD

The present invention relates to organically modified metal oxide nanoparticles that can be used as a photoresist material used in a semiconductor manufacturing process or the like, a method for producing the same, an EUV photoresist material, and a method for producing an etching mask.

BACKGROUND ART

In recent years, semiconductor circuit patterns have become thinner, accelerating the research and development of lithography using extreme ultraviolet light (EUV). With the thinning of the pattern, the resist film used for pattern formation has become thinner. Therefore, a resist material having resistance to etching is required. Inorganic substances such as metal oxides have been studied as resist materials having etching resistance.

Methods using nanoparticles of oxides of metal such as zirconium or hafnium organically modified with a carboxylic acid such as methacrylic acid (hereinafter referred to as "MAA") as a resist material have been proposed (PTLs 1 and 2). Since the metal oxide nanoparticles have a metal oxide in the core, the resist materials containing the metal oxide nanoparticles have higher resistance to etching and sensitivity to EUV light as compared with resist materials of organic substances. Furthermore, due to the high symmetry of the structure of the metal oxide nanoparticles, the metal oxide nanoparticles are unlikely to remain as insoluble matter on the wafer when the resist material containing the metal oxide nanoparticles is developed.

Further, methods using a complex (monomer or salt) of metal such as zirconium or hafnium and an organic substance represented by a carboxylic acid such as methacrylic acid as a resist material have also been proposed (PTLs 3 to 5). Since the size of the complex of organic substance itself is small, the resist material is suitable for thinning as compared with resist materials containing a nanoparticle core. However, the resist material forms a film having a higher percentage of organic substance than the resist material containing nanoparticle as the core. Therefore, the resist material has low resistance to etching. Furthermore, due to the low symmetry of the structure of the organic substance complex, the complex of organic substance is likely to remain as an insoluble matter on the wafer when the resist material containing the complex of organic substance is developed.

Citation List

Patent Literature

[PTL 1]
Japanese Unexamined Patent Publication First Publication No. 2017-173537
[PTL 2]
Japanese Unexamined Patent Publication First Publication No. 2015-157807
[PTL 3]
Japanese Unexamined Patent Publication First Publication No. 2015-108781
[PTL 4]
Japanese Unexamined Patent Publication First Publication No. 2012-185484
[PTL 5]
Japanese Unexamined Patent Publication First Publication No. 2001-072716

SUMMARY OF INVENTION

Technical Problem

In view of the above, the synthesis of organically modified metal oxide nanoparticles with a small core diameter is important for the development of resist materials to form fine patterns. Generally, organically modified metal oxide nanoparticles having a small core diameter are produced by mixing a metal alkoxide such as zirconium and an organic substance such as methacrylic acid in a non-aqueous solvent in an extremely low humidity environment. However, alkoxides are expensive, and expensive equipment such as a glove box needs to be installed and maintained in order to achieve an extremely low humidity environment. Therefore, organically modified metal oxide nanoparticles having a small core diameter have a problem in terms of manufacturing cost.

Furthermore, the reaction mechanism of the resist material during EUV exposure and the exposure operating factors are not yet clear, and the establishment of a method to control the sensitivity and resolution of the resist material is required. The adjustment of sensitivity and resolution is often performed by optimizing the solvent and additives of the resist solution and developer. However, if the sensitivity and resolution of the resist material can be adjusted by controlling the structure of the material itself, more specifically, by modifying with a plurality of modification groups and controlling the composition thereof, it becomes possible to examine a more diversified method for adjusting the resist material.

The present invention has been made in view of such circumstances, and an object thereof is to provide organically modified metal oxide nanoparticles that can be produced by a simple method and can increase the sensitivity and resolution of a resist material, a method for producing the same, an EUV photoresist material, and a method for producing an etching mask.

Solution to Problem

When a resist material is irradiated with EUV, the reactivity of organically modified metal oxide nanoparticles constituted by a metal oxide and a carboxylic acid contained in the resist material, that is, the sensitivity, and the resolution of the formed resist pattern greatly vary depending on the kind of ligands, such as carboxylic acids, to be coordinated. The present inventors have found that by coordinating two or more kinds of carboxylic acids having different molecular weights to the metal oxide core portion, the reactivity (sensitivity) is improved when a resist material containing the organically modified metal oxide nanoparticles is irradiated with EUV, that is, the solubility in the developer is reduced, while maintaining the solubility of the obtained organically modified metal oxide nanoparticles in the resist solvent and the developer.

In addition, the present inventors have also found that when a resist material containing organically modified metal oxide nanoparticles obtained by coordinating a carboxylic acid and an inorganic anion smaller in size than the carboxylic acid to a metal oxide core portion is formed into a film, the organically modified metal oxide nanoparticles are closely packed and the resolution of the resist film is improved.

Organically modified metal oxide nanoparticles of the present invention have a core including a plurality of metal atoms and a plurality of oxygen atoms bonded to the plurality of metal atoms, and a first modification group which is a carboxylic acid carboxylate ligand coordinated to the core, and a second modification group which is at least one of the group consisting of a carboxylic acid carboxylate ligand coordinated to the core and having a smaller molecular weight than the first modification group and an inorganic anion smaller in size than the first modification group.

An EUV photoresist material of the present invention contains the organically modified metal oxide nanoparticles of the present invention and a solvent.

A method for producing organically modified metal oxide nanoparticles of the present invention includes a reaction step of reacting a metal oxynitrate (an oxo-metal nitrate) and/or a metal oxyacetate (an oxo-metal acetate) with methacrylic acid in a hydrophilic liquid. A method for producing an etching mask of the present invention includes a film forming step of applying the EUV photoresist material of the present invention onto a layer to be etched and drying the EUV photoresist material to obtain a resist film, an exposure step of irradiating the resist film with EUV in a predetermined pattern, and a developing step of removing a portion not irradiated with EUV in the exposure step to form an etching opening.

Advantageous Effects of Invention

According to the organically modified metal oxide nanoparticles, the method for producing organically modified metal oxide nanoparticles, and the EUV photoresist material of the present invention, a resist material that can be produced by a simple method and has high sensitivity and resolution can be obtained. Further, according to the method for producing an etching mask of the present invention, a mask can be thinned by using the EUV photoresist material.

DESCRIPTION OF EMBODIMENTS

Figure 1:
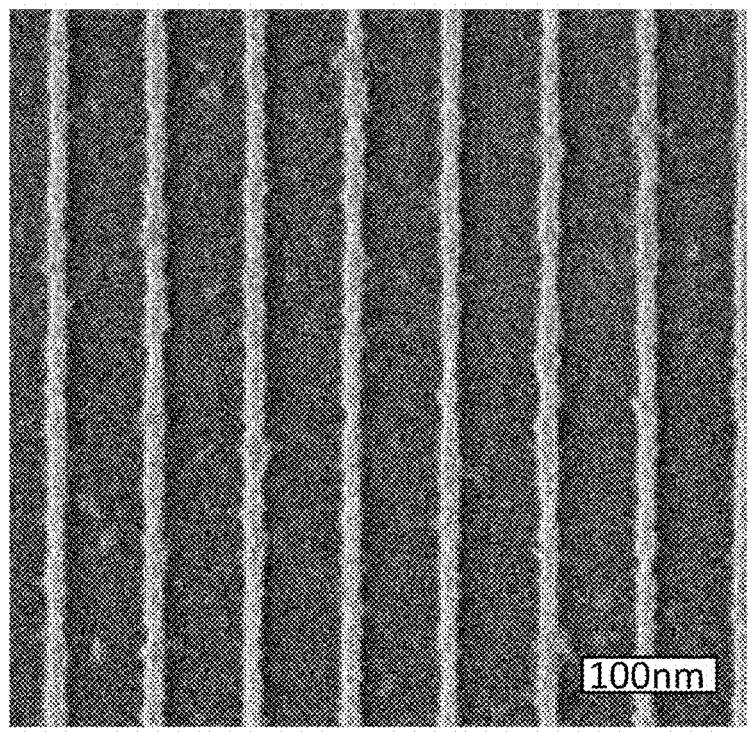
FIG. 1 is an SEM image of a silicon wafer obtained in Example 1.

Organically modified metal oxide nanoparticles according to an embodiment of the present invention include a core, a first modification group, and a second modification group. The core includes a plurality of metal atoms and a plurality of oxygen atoms bonded to the plurality of metal atoms. The first modification group is a carboxylic acid carboxylate ligand coordinated to the core. The second modification group is a carboxylic acid carboxylate ligand coordinated to the core and having a smaller molecular weight than the first modification group and/or an inorganic anion smaller in size than the first modification group.

The first modification group is preferably a methacrylic acid carboxylate ligand because the organically modified metal oxide nanoparticles are easily soluble in propylene glycol 1-monomethyl ether 2-acetate, (PGMEA) which is a general-purpose resist solvent, and the reactivity of the organically modified metal oxide nanoparticles upon irradiation with EUV is improved. The metal is preferably one or more selected from the group consisting of Zr (zirconium), Hf (hafnium), and Ti (titanium), and more preferably Zr. The second modification group is preferably at least one of the group consisting of an acetic acid carboxylate ligand and a nitrate ion.

The organically modified metal oxide nanoparticles of the present embodiment are preferably represented by General formula $M_6O_4(OH)_4X_nY_{12-n}$. Here, M is a metal and is one or more selected from the group consisting of Zr, Hf, and Ti, X is the first modification group, Y is the second modification group, and $1 \leq n \leq 11$ is satisfied. Further, Z defined by $X/(X+Y) \times 100$, which represents the ratio of X and Y, preferably satisfies the relationship of 5 mol % $\leq Z \leq$ 95 mol %.

The size of the carboxylic acid carboxylate ligand which is the first modification group is, for example, 0.52 nm, and the size of the inorganic anion which is the second modification group is, for example, 0.33 nm. By comparing the above values, it can be confirmed that the size of the inorganic anion which is the second modification group is smaller than the size of the carboxylic acid carboxylate ligand which is the first modification group.

An EUV photoresist material according to an embodiment of the present invention contains the organically modified metal oxide nanoparticles of the present embodiment and a solvent. Examples of the solvent include butyl acetate, PGMEA, methanol, ethanol, and propanol. The EUV photoresist material of the present embodiment may further contain a dispersant such as a carboxylic acid, a stabilizer, and a photoresponsive agent such as a photoacid generator.

A method for producing organically modified metal oxide nanoparticles according to an embodiment of the present invention includes a reaction step of reacting at least one of a metal oxynitrate (an oxo-metal nitrate) and a metal oxyacetate (an oxo-metal acetate) with methacrylic acid in a hydrophilic liquid. Examples of the hydrophilic liquid include water, methanol, ethanol, propanol, and acetone. The reaction step may be carried out in an air atmosphere. Therefore, no equipment is required to realize an extremely low humidity environment.

An example of a method for producing organically modified metal oxide nanoparticles using metal oxynitrate (oxo-metal nitrate) will be described. Methacrylic acid is added to an aqueous solution of metal oxynitrate (oxo-metal nitrate), and if necessary, the mixture is stirred, and the obtained precipitate is collected by filtration and dried. In this way, the organically modified metal oxide nanoparticles of the present embodiment can be obtained by a simple method. When X is methacrylic acid carboxylate and Y is nitrate ion, the organically modified metal oxide nanoparticles preferably satisfy the relationship of 50 mol % $\leq Z \leq$ 84 mol %.

Further, the metal oxynitrate (oxo-metal nitrate) is preferably zirconium oxynitrate (oxo-zirconium nitrate).

In addition, an example of a method for producing organically modified metal oxide nanoparticles using metal oxyacetate (oxo-metal acetate) will be described. Methacrylic acid is added to an aqueous solution of metal oxyacetate (oxo-metal acetate), and if necessary, the mixture is stirred, and the obtained precipitate is collected by filtration and dried. In this way, the organically modified metal oxide nanoparticles of the present embodiment can be obtained by a simple method. When X is methacrylic acid carboxylate and Y is acetic acid carboxylate, the organically modified metal oxide nanoparticles preferably satisfy the relationship of 58 mol % ≤Z≤92 mol %. Further, the metal oxyacetate (oxo-metal acetate) is preferably zirconium oxyacetate (oxo-zirconium acetate).

A method for producing an etching mask according to an embodiment of the present invention includes a film forming step, an exposure step, and a developing step. In the film forming step, the EUV photoresist material of the present embodiment is applied onto a layer to be etched and dried to obtain a resist film. The type of the layer to be etched is not particularly limited. Examples of the layer to be etched includes a silicon layer, a silicon oxide layer, or a silicon nitride layer.

In the exposure step, the resist film is irradiated with EUV in a predetermined pattern. In the developing step, the portion not irradiated with EUV in the exposure step is removed to form an etching opening. In the developing step, for example, the resist film is immersed in a developer such as butyl acetate, and the portion not irradiated with EUV is dissolved in the developer and removed. By using the EUV photoresist material of the present embodiment, the width of the etching mask can be reduced to 20 nm or less. Therefore, the layer to be etched can be finely etched.

EXAMPLES

Example 1

An aqueous solution of zirconium oxynitrate (oxo-zirconium nitrate) was prepared by dissolving 1.2 g of zirconium oxynitrate (oxo-zirconium nitrate) in 3 mL of a 5.0 M aqueous nitric acid solution. Into 1 mL of the zirconium oxynitrate (oxo-zirconium nitrate) aqueous solution, 1 mL of methacrylic acid was added, and the mixture was stirred for 5 minutes and then allowed to stand at room temperature for 5 days. The obtained precipitate was collected by filtration under decompression and vacuum dried at room temperature for 1 day to obtain a white powder. As a result of elemental analysis of the white powder, the carbon and nitrogen contents were found to be 20.5 wt % and 3.8 wt %, respectively. The ratio of amount of substance (so-called mol ratio) was methacrylic acid: nitric acid=61: 39=7.3:4.7. As a result of thermogravimetric analysis of the white powder, the weight loss rate was found to be 54%. Further, the size of methacrylic acid was about 0.52 nm, and the size of nitrate ion was about 0.33 nm.

As a result of IR analysis of the white powder, an absorption peak derived from the carboxy group (1558 $cm^{-1}$) and an absorption peak of the stretching vibration band of C=C (1647 $cm^{-1}$) of methacrylic acid, and an absorption peak of the out-of-plane bending vibration band of the vinyl group CH (827 $cm^{-1}$) were confirmed. In addition, as a result of matrix-assisted laser desorption/ionization time-of-flight mass spectrometry (MALDI-TOF/MS) of the white powder, peaks were found at m/z 1456, 1588, 1611, and 1719, which are almost equal to the molecular weight of zirconia hexamer with some missing methacrylic acid ligands. From the above, it is considered that the obtained white powder is $Zr_6O_4(OH)_4(MAA)_{7.3}(NO_3)_{4.7}$.

In 5.0 g of PGMEA, 0.2 g of the white powder was dissolved. The undissolved white powder was removed using centrifugation and a filter with a pore size of 0.45 μm. As a result of dynamic light scattering analysis of the solution after the removal, the volume-based average particle size of the white powder was found to be about 2 nm. From this result, it can be considered that the obtained white powder is organically modified metal oxide nanoparticles in which methacrylic acid and nitric acid are coordinated with respect to the core constituted by zirconium and oxygen.

PGMEA was further added to the solution and diluted twice to obtain a solution A for EUV exposure. The solution A for EUV exposure was dropped onto a silicon wafer and rotated at 1500 rpm for 60 seconds to form a film, and then heated at 80° C. for 60 seconds to obtain a resist film A. The film thickness of the resist film A was measured with a spectroscopic ellipsometer and found to be 20 nm. The resist film A was exposed to EUV with an irradiation amount of 12 to 76 mJ/$cm^2$ through a predetermined pattern, and then immersed in butyl acetate for 30 seconds for development to remove the EUV non-irradiated portion of the resist film A.

The silicon wafer after development was observed by SEM. FIG. 1 shows an SEM image of the developed silicon wafer when EUV exposure was performed at an irradiation amount of 52 mJ/$cm^2$. As shown in FIG. 1, the line width of the insolubilized resist film A (light-colored portion), which is an etching mask remaining on the silicon wafer (dark-colored portion), was 18 nm, which is narrower than that in Comparative Example 1 described later, formation of nano-patterning with high resolution was confirmed.

Example 2

After adding 2 mL of methacrylic acid to 1 mL of a 20 wt % zirconium oxyacetate (oxo-zirconcium acetate) aqueous solution, the mixture was stirred at room temperature for 1 hour. The obtained precipitate was collected by filtration under decompression and vacuum dried at room temperature for 1 day to obtain a white powder. As a result of elemental analysis of the white powder, the carbon content was found to be 29 wt %. In addition, as a result of thermogravimetric analysis of the white powder, the weight loss rate was found to be 52%. Furthermore, as a result of IR analysis of the white powder, an absorption peak derived from the carboxy group and an absorption peak of the stretching vibration band of C=C (1647 $cm^{-1}$) of methacrylic acid (1558 $cm^{-1}$), and an absorption peak of the out-of-plane bending vibration band of the vinyl group CH (827 $cm^{-1}$) were confirmed.

As a result of matrix-assisted laser desorption/ionization time-of-flight mass spectrometry (MALDI-TOF/MS) of the white powder, peaks were found at m/z 1595 and 1704, which are almost equal to the molecular weight of zirconia hexamer with a methacrylic acid ligand and an acetic acid ligand, and the molecular weight of the zirconia hexamer with some missing ligands thereof. As a result of $^1$H-NMR analysis of the white powder dissolved in the solvent, the ratio of amount of the substance was found to be methacrylic acid: acetic acid=87:13=10.4:1.6. From the above, it is considered that the obtained white powder is $Zr_6O_4(OH)_4(MAA)_{10.4}Ac_{1.6}$ on average.

In 2.0 g of PGMEA, 0.06 g of the white powder was dissolved. The undissolved white powder was removed using centrifugation and a filter with a pore size of 0.45 μm. As a result of dynamic light scattering analysis of the solution after the removal, the volume-based average particle size of the white powder was found to be about 2 nm. From this result, it can be considered that the obtained white powder is organically modified metal oxide nanoparticles in which methacrylic acid and acetic acid are coordinated with respect to the core constituted by zirconium and oxygen.

PGMEA was further added to the solution and diluted twice to obtain a solution B for EUV exposure. The solution B for EUV exposure was dropped onto a silicon wafer and rotated at 1500 rpm for 60 seconds to form a film, and then heated at 80° C. for 60 seconds to obtain a resist film B. The film thickness of the resist film B was measured with a spectroscopic ellipsometer and found to be 20 nm. The resist film B was exposed to EUV with an irradiation amount of 7 to 39 mJ/cm$^2$ through a predetermined pattern, and then immersed in butyl acetate for 30 seconds for development to remove the EUV non-irradiated portion of the resist film B.

Figure 2:
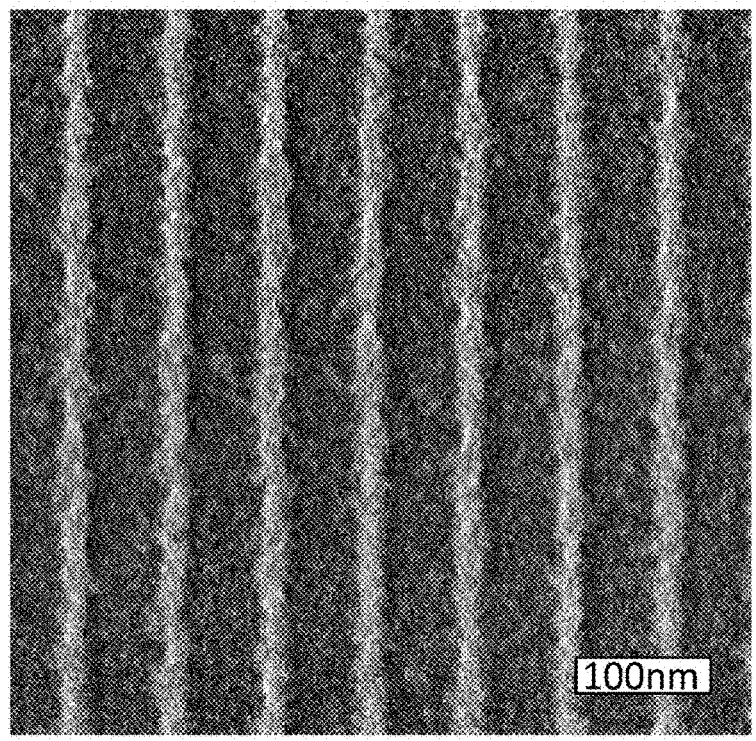
FIG. 2 is an SEM image of a silicon wafer obtained in Example 2.

The silicon wafer after development was observed by SEM. FIG. 2 shows an SEM image of a silicon wafer after development when EUV exposure was performed at a low irradiation amount of 22 mJ/cm$^2$, that is, under the condition that high sensitivity is required for the resist film. As shown in FIG. 2, the line width of the insolubilized resist film B (light-colored portion), which is an etching mask remaining on the silicon wafer (dark-colored portion), was 23 nm, formation of nano-patterning with high sensitivity at an irradiation amount lower than that in Comparative Example 1 described later was confirmed.

Example 3

A beaker A containing 5 mL of a 20 wt % zirconium oxyacetate (oxo-zirconium acetate) aqueous solution and a beaker B containing 10 mL of methacrylic acid were placed in a closed container and left at room temperature for 7 days. The vapor of methacrylic acid was gradually dissolved in the zirconium oxyacetate (oxo-zirconium acetate) aqueous solution to obtain a precipitate in the beaker A. The precipitate was collected by filtration under decompression and vacuum dried at room temperature for 1 day to obtain a white powder. As a result of IR analysis of the white powder, an absorption peak derived from the carboxy group (1558 cm$^{-1}$) and an absorption peak of the stretching vibration band of C=C (1647 cm$^{-1}$) of methacrylic acid, and an absorption peak of the out-of-plane bending vibration band of the vinyl group CH (827 cm$^{-1}$) were confirmed.

As a result of $^1$H-NMR analysis of the white powder dissolved in the solvent, the ratio of the amount of substance was found to be methacrylic acid: acetic acid=34:66=4.1:7.9. From the above, it is considered that the obtained white powder is $Zr_6O_4(OH)_4(MAA)_{4.1}Ac_{7.9}$ on average.

Comparative Example 1

In a glovebox, 1.02 g of methacrylic acid was added to 1.40 g of 85% zirconium butoxide solution in 1-butanol. Then, the mixture was stirred and allowed to stand for about 3 weeks to obtain a single crystal of $Zr_6O_4(OH)_4(MAA)_{12}$. The single crystal was collected by filtration under decompression, vacuum dried at room temperature for 1 day, and pulverized to obtain a white powder. As a result of elemental analysis of the white powder, the carbon content was found to be 36 wt %. As a result of thermogravimetric analysis of the white powder, the weight loss rate was found to be 57%.

In addition, as a result of IR analysis of the white powder, an absorption peak derived from the carboxy group (1558 cm$^{-1}$) and an absorption peak of the stretching vibration band of C=C (1647 cm$^{-1}$) of methacrylic acid, and an absorption peak of the out-of-plane bending vibration of the vinyl group CH (827 cm$^{-1}$) were confirmed. Furthermore, as a result of matrix-assisted laser desorption/ionization time-of-flight mass spectrometry (MALDI-TOF/MS) of the white powder, a peak was found at m/z 1702, which is almost equal to the molecular weight of zirconia hexamer coordinated with methacrylic acid. From the above, it is considered that the obtained white powder is $Zr_6O_4(OH)_4(MAA)_{12}$ on average.

In 3.0 g of PGMEA, 0.09 g of the white powder was dissolved. The undissolved white powder was removed using centrifugation and a filter with a pore size of 0.45 μm. As a result of dynamic light scattering analysis of the solution after the removal, the volume-based average particle size of the white powder was found to be about 2 nm. From this result, it can be considered that the obtained white powder is organically modified metal oxide nanoparticles in which methacrylic acid is coordinated with respect to the core constituted by zirconium and oxygen. PGMEA was further added to the solution and diluted twice to obtain a solution C for EUV exposure. The solution C for EUV exposure was dropped onto a silicon wafer and rotated at 1500 rpm for 60 seconds to form a film, and then heated at 80° C. for 60 seconds to obtain a resist film C. The film thickness of the resist film C was measured with a spectroscopic ellipsometer and found to be 20 nm.

Figure 3:
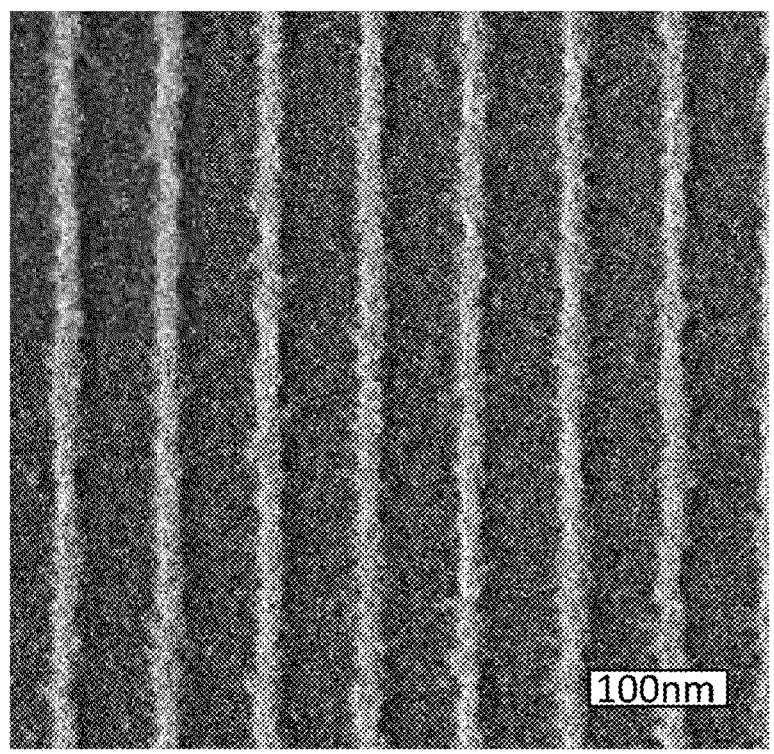
FIG. 3 is an SEM image of a silicon wafer obtained in Comparative Example 1.

The resist film C was exposed to EUV with an irradiation amount of 28 to 60 mJ/cm$^2$ through a predetermined pattern, and then immersed in butyl acetate for 30 seconds for development to remove the EUV non-irradiated portion of the resist film C. The silicon wafer after development was observed by SEM. FIG. 3 shows an SEM image of the developed silicon wafer when EUV exposure was performed at an irradiation amount of 46 mJ/cm$^2$. As shown in FIG. 3, the line width of the insolubilized resist film C (light-colored portion), which is an etching mask remaining on the silicon wafer (dark-colored portion), was 21 nm.

Example 4

In a glovebox, 0.9 mL of methacrylic acid, which is the raw material of the second modification group, and 1.1 mL of isobutyric acid, which is the raw material of the first modification group were added to 1.63 mL of 80% zirconium butoxide solution in 1-butanol. Then, the mixture was stirred for about 7 days to obtain a white precipitate. The white precipitate was collected by filtration under decompression, vacuum dried at room temperature for 1 day, and pulverized to obtain a white powder. As a result of $^1$H-NMR analysis of the white powder dissolved in the solution, the ratio of amount of substance was found to be methacrylic acid: isobutyric acid=7:3. In 5.0 g of PGMEA, 0.15 g of the white powder was dissolved. As a result of dynamic light scattering analysis of the solution, the volume-based average particle size of the white powder was found to be about 1 nm. From the above, it is considered that the obtained white powder is organically modified metal oxide nanoparticles in which methacrylic acid and isobutyric acid are coordinated with respect to the core constituted by zirconium and oxygen.

The solution was dropped onto a silicon wafer and rotated at 1500 rpm for 60 seconds to form a film, and then heated at 80° C. for 60 seconds to obtain a resist film. The resist film was exposed to EUV with an irradiation amount of 0 to 25 mJ/cm$^2$, then immersed in butyl acetate for 30 seconds for development, dried, and then the film thickness was measured with a spectroscopic ellipsometer. As a result, a film insolubilized at an irradiation amount of 15 mJ/cm$^2$ or more remained, and the film thickness increased with an increase in the irradiation amount, and at 25 mJ/cm$^2$, the film thickness became about 17 nm, confirming the reactivity with EUV exposure.

Example 5

In a glovebox, 1 mL of methacrylic acid, which is the raw material of the first modification group, and 1 mL of propionic acid, which is the raw material of the second modification group were added to 1.63 mL of 80% zirconium butoxide solution in 1-butanol. Then, the mixture was stirred for about 5 days to obtain a white precipitate. The white precipitate was collected by filtration under decompression, vacuum dried at room temperature for 1 day, and pulverized to obtain a white powder. As a result of $^1$H-NMR analysis of the white powder dissolved in the solution, the ratio of amount of substance was found to be methacrylic acid: propionic acid=7: 3. In 5.0 g of PGMEA, 0.15 g of the white powder was dissolved. As a result of dynamic light scattering analysis of the solution, the volume-based average particle size of the white powder was found to be about 2 nm. From the above, it is considered that the obtained white powder is organically modified metal oxide nanoparticles in which methacrylic acid and propionic acid are coordinated with respect to the core constituted by zirconium and oxygen.

The solution was dropped onto a silicon wafer and rotated at 1500 rpm for 60 seconds to form a film, and then heated at 80° C. for 60 seconds to obtain a resist film. The resist film was exposed to EUV with an irradiation amount of 0 to 25 mJ/cm$^2$, then immersed in butyl acetate for 30 seconds for development, dried, and then the film thickness was measured with a spectroscopic ellipsometer. As a result, a film insolubilized at an irradiation amount of 5 mJ/cm$^2$ or more remained, and the film thickness increased with an increase in the irradiation amount, and at 25 mJ/cm$^2$, the film thickness became about 40 nm, confirming the reactivity with EUV exposure.

Example 6

In a glovebox, 1 mL of methacrylic acid, which is the raw material of the second modification group, and 1 mL of butyric acid, which is the raw material of the first modification group were added to 1.63 mL of 80% zirconium butoxide solution in 1-butanol. Then, the mixture was stirred for about 5 days to obtain a white precipitate. The white precipitate was collected by filtration under decompression, vacuum dried at room temperature for 1 day, and pulverized to obtain a white powder. As a result of $^1$H-NMR analysis of the white powder dissolved in the solution, the ratio of amount of substance was found to be methacrylic acid: isobutyric acid=2: 1. In 5.0 g of PGMEA, 0.15 g of the white powder was dissolved. As a result of dynamic light scattering analysis of the solution, the volume-based average particle size of the white powder was found to be about 2 nm. From the above, it is considered that the obtained white powder is organically modified metal oxide nanoparticles in which methacrylic acid and butyric acid are coordinated with respect to the core constituted by zirconium and oxygen.

The solution was dropped onto a silicon wafer and rotated at 1500 rpm for 60 seconds to form a film, and then heated at 80° C. for 60 seconds to obtain a resist film. The resist film was exposed to EUV with an irradiation amount of 0 to 25 mJ/cm$^2$, then immersed in butyl acetate for 30 seconds for development, dried, and then the film thickness was measured with a spectroscopic ellipsometer. As a result, a film insolubilized at an irradiation amount of 9 mJ/cm$^2$ or more remained, and the film thickness increased with an increase in the irradiation amount, and at 25 mJ/cm$^2$, the film thickness became about 33 nm, confirming the reactivity with EUV exposure.

What is claimed is:

1. Organically modified metal oxide nanoparticles including a plurality of organically modified metal oxide nanoparticles, each organically modified metal oxide nanoparticle comprising:
    a core including a plurality of metal atoms and a plurality of oxygen atoms bonded to the plurality of metal atoms;
    a first modification group which is a carboxylic acid carboxylate ligand coordinated to the core;
    a second modification group which is a carboxylic acid carboxylate ligand coordinated to the core and having a smaller molecular weight than the first modification group and/or an inorganic anion smaller in size than the first modification group,
    wherein each nanoparticle is represented by general formula $M_6O_4(OH)_4X_nY_{12-n}$,
    provided that M is the metal atom and is one or more selected from the group consisting of Zr, Hf, and Ti, X is the first modification group, Y is the second modification group, and $1 \leq n \leq 11$ is satisfied, and
    X and Y of the general formula satisfies a relationship 5 mol % $\leq$ X/(X+Y)×100 $\leq$ 95 mol %.

2. The organically modified metal oxide nanoparticles according to claim 1, wherein the first modification group is a methacrylic acid carboxylate ligand and the second modification group is an acetic acid carboxylate ligand and/or nitrate ion.

3. The organically modified metal oxide nanoparticles according to claim 1,
    wherein the metal is Zr.

4. An EUV photoresist material comprising:
    the organically modified metal oxide nanoparticles according to claim 1; and
    a solvent.

5. A method for producing organically modified metal oxide nanoparticles according to claim 1, the method comprising a reaction step of reacting a metal oxynitrate (an oxo-metal nitrate) and/or a metal oxyacetrate (an oxo-metal acetate) with methacrylic acid in a hydrophilic liquid to obtain organically modified metal oxide nanoparticles in each of which carboxylic acid carboxylate ligand and inorganic ion are coordinated to a core comprising a plurality of metal and a plurality of oxygen atoms bonded to the plurality of metals.

6. The method for producing organically modified metal oxide nanoparticles according to claim 5,
    wherein the reaction step is carried out in an air atmosphere.

7. The method for producing organically modified metal oxide nanoparticles according to claim 5,
    wherein the metal oxynitrate (oxo-metal nitrate) is zirconium oxynitrate (oxo-zirconium nitrate) and the metal oxyacetate (oxo-metal acetate) is zirconium oxyacetate (oxo-zirconium acetate).

8. A method for producing an etching mask, comprising:
a film forming step of applying the EUV photoresist material according to claim 4 onto a layer to be etched and drying the EUV photoresist material to obtain a resist film;
an exposure step of irradiating the resist film with EUV in a predetermined pattern; and
a developing step of removing a portion not irradiated with EUV in the exposure step to form an etching opening.

9. The organically modified metal oxide nanoparticles according to claim 1,
wherein X is methacrylic acid carboxylate and Y is acetic acid carboxylate, and
wherein X and Y of the general formula satisfies a relationship 50 mol %≤X/(X+Y)×100≤84 mol %.

10. The organically modified metal oxide nanoparticles according to claim 1,
wherein X is methacrylic acid carboxylate and Y is nitrate ion, and
wherein X and Y of the general formula satisfies a relationship 50 mol %≤X/(X+Y)×100≤84 mol %.

11. The organically modified metal oxide nanoparticles according to claim 1,
wherein the second modification group comprises an inorganic anion smaller in size than the first modification group.

12. The organically modified metal oxide nanoparticles according to claim 1,
wherein the second modification group comprises nitrate ion.

13. The organically modified metal oxide nanoparticles according to claim 1,
wherein the second modification group is nitrate ion.

* * * * *